United States Patent [19]

Padley

[11] Patent Number: 5,508,048
[45] Date of Patent: Apr. 16, 1996

[54] ENZYMATIC TRANSESTERIFICATION STARTING FROM HIGH ERUCIC CRUCIFERAE OILS

[75] Inventor: Frederick B. Padley, Bedford, Netherlands

[73] Assignee: Van Den Bergh Foods Co., New York, N.Y.

[21] Appl. No.: 178,633

[22] Filed: Jan. 7, 1994

Related U.S. Application Data

[63] Continuation of Ser. No. 874,995, Apr. 24, 1992, abandoned, which is a continuation of Ser. No. 604,029, Oct. 24, 1990, abandoned.

[30] Foreign Application Priority Data

Nov. 9, 1989 [GB] United Kingdom ............... 8925352

[51] Int. Cl.$^6$ .................................................. A23D 7/00
[52] U.S. Cl. ...................... 426/33; 426/47; 426/601; 426/607; 435/72; 435/134; 435/135; 554/148; 554/157; 554/169
[58] Field of Search ................. 426/33, 417, 601, 426/607, 47; 435/72, 134, 135; 554/148, 157, 169

[56] References Cited

U.S. PATENT DOCUMENTS

| | | | |
|---|---|---|---|
| 2,182,332 | 12/1939 | Barsky. | |
| 4,275,081 | 6/1981 | Coleman et al. | 426/33 |
| 4,705,692 | 11/1987 | Tanaka et al. | 426/607 |
| 4,726,959 | 2/1988 | Momura et al. | 426/607 |
| 4,839,192 | 6/1989 | Sagi et al. | 426/607 |
| 4,839,287 | 6/1989 | Holmberg et al. | 435/135 |
| 4,873,109 | 10/1989 | Tanaka et al. | 426/607 |
| 4,877,636 | 10/1989 | Koyano et al. | 426/607 |
| 4,985,358 | 1/1991 | Sawamura et al. | 435/134 |

FOREIGN PATENT DOCUMENTS

| | | | |
|---|---|---|---|
| 0079986 | 6/1983 | European Pat. Off.. | |
| 0233036 | 8/1987 | European Pat. Off. | A23D 3/00 |
| 0276548 | 6/1990 | European Pat. Off.. | |
| 62-118848 | 5/1987 | Japan. | |
| 63-240790 | 10/1988 | Japan. | |
| 01157342 | 6/1989 | Japan. | |
| 0235039 | 2/1990 | Japan. | |
| 0265744 | 3/1990 | Japan. | |
| 867852 | 5/1961 | United Kingdom. | |
| 1577933 | 10/1980 | United Kingdom | C11C 3/10 |
| 2185990 | 8/1987 | United Kingdom. | |

OTHER PUBLICATIONS

Gunstone, D. The Lipid Handbook, p. 82, Chapman and Hall, London.

Kaimal et al., Modification of Vegetable Oils by Lipase Catalyzed Interesterification, Journal of the Oil Technologists' Association of India, No. 1, Jan.–Mar., 1989, pp. 2–10.

Swern, D. ed., Bailey's Industrial Oil and Fat Products vol. 1, 1979, p. 416, John Wiley & Sons, New York.

*Primary Examiner*—Leslie Wong
*Attorney, Agent, or Firm*—Cushman Darby & Cushman

[57] ABSTRACT

High erucic cruciferae oils are interesterified with $C_{16}$ or higher fatty acids or derivatives thereof. The use of a 1,3-selective lipase leads to the introduction of the fatty acid groups in the 1,3-positions. The liberated erucic acid (derivative) can be hydrogenated; the behenyl acid (or derivative) thus formed can be recirculated to provide at least 50% of the behenyl acid (derivative) needed in the process. The products obtainable by these processes, display good anti-blooming properties.

5 Claims, No Drawings

ENZYMATIC TRANSESTERIFICATION STARTING FROM HIGH ERUCIC CRUCIFERAE OILS

This is a continuation of application No. 07/874,995, filed on Apr. 24, 1992, which was abandoned upon the filing hereof which is a continuation of Ser. No. 07/604,029, filed Oct. 24, 1990, now abandoned.

BACKGROUND OF THE INVENTION

This invention relates to a novel preparation of triglycerides by rearrangement under the influence of lipase enzymes of rapeseed oils.

The rearrangement of fats and oils under the influence, as rearrangement catalyst, of lipase enzymes in a substantially non-aqueous medium has already been disclosed in our British patent specification N° 1577933. Under the influence of the catalyst, the fatty acid residues of the triglycerides, of which glyceride oils and fats are largely composed, may be rearranged selectively or non-selectively according to the characteristics of the catalyst. Different fatty acid residues may be introduced into a particular triglyceride from another triglyceride or from free fatty acid or alkyl ester thereof included in the reaction medium, which is conducted in liquid phase in the presence or absence of added solvent, which should be water-immiscible, although a small amount of water is introduced with the catalyst and may also be present in the reaction medium to maintain the activity of the catalyst.

It has already been proposed in EP 233,036 to prepare saturated triglycerides containing $C_{14}$ and shorter-chain fatty acids by rearrangement with such acids or their alkyl esters of vegetable oils, including rapeseed oil, in the presence of 1,3-selective lipase enzymes as rearrangement catalysts, the oil or the rearranged product being saturated by hydrogenation.

An important aspect of the 1,3-selective lipase rearrangement process is the conversion of cheap vegetable oils containing a high proportion of unsaturated fatty acid residues to symmetrical disaturated triglycerides of stearic and palmitic and higher fatty acids, of which cocoa butter and other expensive vegetable butters are largely composed, to provide fats replicating the melting profiles, for which vegetable butters are highly prized, for use in chocolate, confectionery generally and non-food applications in the pharmaceutical industry.

The source of feedstock for lipase rearrangement processes imposes some limitations on the characteristics of the rearrangement product where the catalyst is selective in action. Thus, a 1,3-selective lipase provides a rearrangement product in which the fatty acids occupying the 1- and 3-positions of its triglycerides are randomly distributed, leaving the 2-position fatty acids unchanged. Where therefore the feedstock consists of highly unsaturated triglycerides, as, for example, in vegetable oils, which are subjected to 1,3-selective rearrangement to obtain symmetrical disaturated triglycerides, these may contain a higher proportion in the 2-position of polyunsaturated fatty acids containing more than one double bond than are found in the corresponding triglycerides of cocoa butter and similar vegetable butters consisting substantially of 2-oleyl triglycerides. It has, however, been proposed to use as feedstock for 1,3-selective rearrangement processes, vegetable oils, e.g. sunflower and safflower oil from seed varieties yielding high oleate oils and thus containing fewer linoleic and more highly unsaturated fatty acids than appears in more familiar varieties. Moreover, whereas palmitic acid, and particularly stearic acid, may be readily obtained from vegetable oils for use in these lipase processes, longer-chain saturated fatty acids, such as arachidic and behenic acids, are less widely available for the preparation of the corresponding 1,3-disaturated triglycerides.

SUMMARY OF THE INVENTION

We have now found that these limitations may be minimized in an improved process for the rearrangement of triglycerides in a rapeseed oil under the influence, as rearrangement catalyst, of a 1,3-selective lipase enzyme and in the presence of a saturated, free fatty acid or derivative thereof, wherein the rearrangement is carried out with a cruciferae oil having a content of erucic acid of at least 20 wt.%, while the fatty acid or derivative thereof has a chain of at least 16 carbon atoms.

Rape, mustard (B. alba, B. nigra) and crambe (Crambe Abyssinica) seed oils all belong to the cruciferae family; they all contain significant quantities of erucic acid which are predominantly in the 1,3-positions, the 2-position being occupied predominantly by unsaturated fatty acids (oleic, linoleic and linolenic acids) [cf. The Lipid Handbook, F. D. Gunstone, J. L. Harwood, F. B. Padley, 1986, p. 52]. Although varieties are known that combine a high 1,3-erucic acid content with a $C_{18}$ polyunsaturated fatty acid content that is less than, and sometimes substantially less than, the oleic acid content, more varieties are known in which the content of polyunsaturated fatty acids in the 2-position is higher than the oleic acid content (e.g. 28% $C_{18:1}$; 41% $C_{18:2}$ and 29% $C_{18:3}$ are very common). So, in contrast to high oleate $C_{16}/C_{18}$ vegetable oils, high oleate rapeseed oils generally contain appreciably more linoleic and linolenic acid in the 2-position, with the result that 1,3-rearranged derivatives contain significantly more 2-linoleoyl and 2-linolenyl triglycerides than are correspondingly produced from the high oleate $C_{16}/C_{18}$ vegetable oils.

An important aspect of the invention is that it benefits from the fact that in high erucic rapeseed oils the erucic acid is enriched at the 1,3-positions, only 3.6% being reported in the 2-position (Brockerhoff 1963).

DETAILED DESCRIPTION OF THE INVENTION

According to a particular feature of the present invention a process is disclosed for the preparation of either mono- or di-behenoyl-2-mono- and poly-unsaturated fatty acid-containing triglycerides comprising selective rearrangement of high erucic cruciferae oil feedstock under the influence, as rearrangement catalyst, of a 1,3-selective lipase enzyme in the presence of behenic acid or a derivative, in particular an alkyl ester thereof, at least part of which is provided by hydrogenating erucic acid or its corresponding alkyl ester separated from the rearrangement product. The reaction products containing behenoyl in the 1- and/or 3-positions and $C_{18}$ polyunsaturated fatty acid residues in the 2-position display anti-blooming behaviour in chocolate compositions. We prefer, however, to use a feedstock that comprises a high erucic seed oil, containing as few polyunsaturated $C_{18}$ fatty acid residues as possible. In this way, a rearranged product is obtained in which the 2-position is predominantly occupied by oleic acid residues. Optionally, residual amounts of dibehenyl triglycerides of $C_{18}$ polyunsaturated fatty acids may be removed from dibehenoyl 2-oleyl triglyceride by a refining process.

In this process, the product obtained after interesterification is separated into a triglyceride-containing fraction and a fraction that contains at least the liberated erucic acid or derivatives thereof.

This can be achieved by any means disclosed in the art (e.g. GB 1,577,933).

In this way, chocolate fat compositions can be obtained that display good anti-blooming properties. These compositions are characterized by the presence of 2–10 wt. %, preferably 5–7 wt. %, of 1,3-dibehenoyl-2-oleyl triglyceride (= BOB); 5–14 wt. %, preferably 7–10 wt. %, of 1,3-dibehenoyl-2–1inoleoyl triglyceride (= BLnB) and 2–10 wt. %, preferably 5–7 wt. %, of 1,3-dibehenoyl-2-linolenyl triglyceride (= BLNB).

The fraction that contains the erucic acid moieties is catalytically hydrogenated. This can be done by known methods (cf., for example, Freifelder, Practical Catalytic Hydrogenation (Techn. and Applications), 1971, pp. 132–134). The preferred catalyst is platinum-on-carbon but Raney nickel also leads to good results. In this way more than 50% of the behenic acid needed in the process can be supplied by the starting material (high 1,3-di-erucic rapeseed oil).

So the normal procedure consists of enzymatic interesterification using a high erucic rapeseed oil-and a behenic acid-containing mixture of fatty acids as reactants. The interesterification is carried out with a 1,3-specific lipase. A solvent, i.e. hexane, is used in order to obtain a liquid. After the interesterification, the diglycerides are removed from the crude reaction products by enzymatic hydrolysis using an enzyme specific for the hydrolysis of diglycerides. The free fatty acids are removed from the reaction product by steam distillation. The fraction containing fatty acids is hydrogenated and the hydrogenated product is recycled. The fraction that contains the triglycerides is wet-fractionated. An olein fraction is separated from a stearin fraction. The olein fraction is recirculated while the stearin fraction is wet-fractionated again. A second stearin fraction consisting mainly of tri-sats is separated from a mid-fraction. The mid-fraction mainly consists of mono- and di-behenoyl triglycerides. This fraction can be used as anti-blooming agent.

EXAMPLE 100 g high erucic rapeseed oil (see Table I) was mixed with 100 g of a fatty acid mixture (obtained by hydrolyzing a hardened rapeseed oil). This mixture was dissolved in 5 l hexane. 50 g enzyme (a 1,3-specific lipase, known as SP-392 ex NOVO) on celite as carrier was added to the mixture.

Interesterification was performed at 60° C. After 1.5 h reaction time, a mixture was obtained in which the triglyceride showed the composition according to Table II (FAME analysis).

TABLE I

|  | High erucic rapeseed FAME | 2-Position | Fatty acids mixture FAME |
|---|---|---|---|
| $C_{14:0}$ | 0.1 | — | 0.1 |
| $C_{16:0}$ | 4.1 | — | 4.0 |
| $C_{16:1}$ | 0.3 | 0.2 | 0.2 |
| $C_{18:0}$ | 1.1 | 0.1 | 46 |
| $C_{18:1}$ | 13.5 | 28.6 | — |
| $C_{18:2}$ | 15 | 41.2 | — |
| $C_{18:3}$ | 10.7 | 29.2 | — |
| $C_{20:0}$ | 9.6 | 0.53 | 4.7 |

TABLE I-continued

|  | High erucic rapeseed FAME | 2-Position | Fatty acids mixture FAME |
|---|---|---|---|
| $C_{22:0}$ | 0.5 | 0.1 | 44 |
| $C_{22:1}$ | 45.1 | 0.9 | — |
| $C_{24}$ | 0.2 | — | 0.6 |

TABLE II

|  | Interesterification product | |
|---|---|---|
|  | FAME | 2-position |
| $C_{14:0}$ | — | — |
| $C_{16:0}$ | 2.7 | — |
| $C_{16:1}$ | 0.1 | 0.5 |
| $C_{18:0}$ | 17.2 | 1.7 |
| $C_{18:1}$ | 9.6 | 27.2 |
| $C_{18:2}$ | 12.8 | 39.2 |
| $C_{18:3}$ | 8.7 | 27.6 |
| $C_{20:0}$ | 5.3 | 0.9 |
| $C_{22:0}$ | 21.9 | 1.5 |
| $C_{22:1}$ | 20.3 | 0.9 |
| $C_{24}$ | 0.7 | — |

The product was subjected to steam distillation. The material containing fatty acids was worked up so as to recover a concentrated mixture of fatty acids. The mixture was hydrogenated, using Pt/C as catalyst. The hydrogenation performance is nearly complete. The hydrogenated acids are recirculated to the interesterification step.

The triglyceride fraction is wet-fractionated, using 6 volumes of acetone per weight unit of triglycerides. The mixture was cooled to −5° C. The stearin fraction was separated from an olein fraction containing solvent. After removal of the solvent, the olein was recirculated. The composition of the stearin fraction is mentioned in Table III.

TABLE III

| Stearin fraction | | |
|---|---|---|
| Tri-sats. | 7.8 | |
| St O St | 7.5 | |
| St Ln St | 10.7 | |
| St LN St | 7.5 | |
| BOB | 5.7 | Total: |
| BLnB | 8.1 | dibehenoyl: |
| BLNB | 5.7 | 19.5% |
| St O B | 12.9 | Total: |
| St Ln B | 18.7 | monobehenoyl: |
| St LN B | 13.1 | 44.7% |
| Others | up to 100% | |

St = Stearic
Ln = Linoleic
LN = Linolenic
O = Oleic

I claim:
1. Process for preparing a 1,3-dibehenoyl triglyceride under the influence, as rearrangement catalyst, of 1,3-selective lipase, comprising
   (a) carrying out the rearrangement with cruciferae oil in the presence of behenic acid or alkyl ester thereof, said oil having an erucic acid content of at least 20wt %, wherein less than 3.6% of erucic acid is bound at the 2-position, the rearrangement being carried out in a solvent selected from the group consisting of water-immiscible solvents and mixtures of water-immiscible solvents with small amounts of water;

(b) separating the 1,3-dibehenoyl triglyceride thus obtained from erucic acid or ester thereof resulting from the rearrangement;

(c) subsequently, hydrogenating the erucic acid or ester thereof thus obtained to form behenic acid; and (d) recirculating the behenic acid obtained in (c) to the rearrangement step (a).

2. Process according to claim 1, wherein the cruciferae oil is a high erucic rapeseed oil.

3. Process according to claim 1, wherein the erucic acid content of the oil is at least 35 wt. %.

4. Process according to claim 2, wherein the high erucic rapeseed oil comprises 2-oleyl groups.

5. The process of claim 1 wherein the behenic acid formed in step (c) constitutes at least 50% of the behenic acid required in step (a).

* * * * *